United States Patent
Wiegmann et al.

(10) Patent No.: US 7,890,179 B2
(45) Date of Patent: Feb. 15, 2011

(54) BONE STIMULATION SYSTEM

(75) Inventors: Markus Wiegmann, Munich (DE); Christian Lutz, Mönkeberg (DE)

(73) Assignee: Stryker Trauma GmbH (DE)

( * ) Notice: Subject to any disclaimer, the term of this patent is extended or adjusted under 35 U.S.C. 154(b) by 915 days.

(21) Appl. No.: 11/583,325

(22) Filed: Oct. 19, 2006

(65) Prior Publication Data

US 2007/0265682 A1 Nov. 15, 2007

(30) Foreign Application Priority Data

May 12, 2006 (EP) .................................. 06009877

(51) Int. Cl.
*A61N 1/05* (2006.01)
(52) U.S. Cl. ....................................................... 607/51
(58) Field of Classification Search .................... 607/51
See application file for complete search history.

(56) References Cited

U.S. PATENT DOCUMENTS

| | | | |
|---|---|---|---|
| 3,745,995 A | 7/1973 | Kraus | |
| 4,195,367 A | 4/1980 | Kraus | |
| 4,421,115 A | 12/1983 | Kraus | |
| 4,430,999 A | 2/1984 | Brighton et al. | |
| 4,549,547 A | 10/1985 | Brighton et al. | |
| 6,778,861 B1 * | 8/2004 | Liebrecht et al. | 607/116 |
| 2004/0254578 A1 | 12/2004 | Vaughan | |
| 2005/0059972 A1 | 3/2005 | Biscup | |
| 2005/0256586 A1 | 11/2005 | Kraus et al. | |

FOREIGN PATENT DOCUMENTS

| | | |
|---|---|---|
| CH | 662279 | 9/1987 |
| DE | 3132488 | 2/1983 |
| WO | WO-2004/082493 | 9/2004 |

OTHER PUBLICATIONS

Opposition to European Patent EP 1854503 B1, Patent Proprietor: Stryker Trauma GmbH, Opponent: Neue Magnetodyn GmbH, dated Aug. 4, 2009.
Response to Opposition to European Patent EP 1854503 B1, Patent Proprietor: Stryker Trauma GmbH, Opponent: Neue Magnetodyn GmbH, dated Jan. 19, 2010.
Summons to attend oral proceedings pursuant to Rule 115(1) EPC, dated May 26, 2010.

* cited by examiner

*Primary Examiner*—Carl H Layno
*Assistant Examiner*—Frances P Oropeza
(74) *Attorney, Agent, or Firm*—Lerner, David, Littenberg, Krumholz & Mentlik, LLP

(57) ABSTRACT

A device for stimulating the osteogenesis of a traumatized bone is mounted on a bone stabilizing implant. The device comprises a first component part comprising a first electrode, an isolating element, which is mounted at the first component part and a second component part comprising a second electrode. The second component part is mounted at the isolating element such that the first electrode and the second electrode are electrically isolated from each other. The power generation unit is electrically coupled both to the first electrode and to the second electrode. The first component part is designed to be attached to the implant in such a manner that the second component part intrudes in a region defined by a trauma within the bone. Further described is a medical system for stimulating the osteogenesis of a traumatized bone, the medical system comprising a bone stabilizing implant, which is adapted to be fixed to the traumatized bone, and an osteogenesis stimulation device as has been described above is mounted thereon.

19 Claims, 2 Drawing Sheets

BONE STIMULATION SYSTEM

BACKGROUND OF THE INVENTION

The present invention relates to the field of stimulating the osteogenesis of a traumatized bone being fixed by means of a bone stabilizing implant. In particular the present invention relates to a device for electrically stimulating the osteogenesis of a traumatized bone being fixed by means of a bone stabilizing implant such as a bone plate or bone nail.

Further, the present invention relates to a medical system for electrically stimulating the osteogenesis of a traumatized bone, wherein the medical system takes benefit from an osteogenesis stimulation device as described above.

It is known that the growth of bone tissue can be promoted by applying an electric field, in particular by a low-frequency alternating field, to the region wherein an improved osteogenesis is desired.

DE 31 32 488 A1 and U.S. Pat. No. 4,195,367 disclose devices for stimulating the bone growth by the method of Kraus-Lechner, which can be used in conjunction with a medullary nail or an osteosynthesis plate. The stimulation devices of DE 31 32 488 comprise a pick-up coil in which a low-frequency alternating voltage can be induced by means of a low-frequency electromagnetic alternating field. Thereby, the voltage is fed to two tissue electrodes one of which may comprise the osteosynthesis implant.

U.S. Pat. No. 6,778,861 B1 discloses a bone screw comprising a device for stimulating bone growth. The bone screw comprises a hollow, tubular shaft consisting of metal, such as titanium, the shaft having a head at one end and an external thread at the other end. The head has a hexagonal recess for inserting a turning tool. An electrically insulated metallic end-piece, which tapers in the direction of the end in the form of a cone or a pointed arch, is inserted into the other end of the shaft. A receiving coil is located in the hollow shaft whereby the terminals of the coil being electrically coupled to the shaft and to the end-piece. The space between the end-piece and the end of the shaft as well as the interior of the shaft are filled with a biocompatible insulating compound. A low-frequency electric voltage can be induced in the receiving coil by an external primary coil, which is coupled to an oscillation generator. The electric voltage generates a growth-promoting current in the surrounding tissue whereby the shaft and the end-piece act as tissue electrodes.

CH 662 279 A5 discloses another device for stimulating bone growth. Thereby, a high-frequency alternating voltage generated by a high-frequency oscillator is amplitude-modulated with the output voltage of a low-frequency oscillator. The amplitude-modulated output voltage of the high-frequency oscillator is applied to outer electrodes of the stimulation device via an impedance-matching transformer and conductors. Two parts of a broken bone are held together mechanically by means of screws. One screw is attached to a metal layer via an insulator and electrically connected to the metal layer via a diode. The metal layer forms an inner electrode. The other screw penetrates a metal plate, which forms a further internal electrode and is connected in an electrically direct fashion to the metal plate. The high-frequency oscillation serves to transmit the low-frequency energy of the low-frequency oscillator to the screws via a capacitor formed by the one external electrode and the one internal electrode as well as a further capacitor formed by the other external electrode and the other internal electrode. The amplitude-modulated high-frequency voltage is demodulated by the diode, such that at the screws the low-frequency voltage required for stimulating the tissue region between the screws is applied to the screws.

U.S. Pat. No. 4,430,999 discloses a cathode assembly for use in conjunction with an internal fracture fixation device for the purpose of stimulating osteogenesis respectively bone growth within a fracture site. The assembly comprises a carrier made from an implantable non-conductive material containing a cathode with a conductive cable leading from the cathode to the patient's electrical bone growth stimulation apparatus. The carrier is mountable on the fixation device for maintenance at the desired location. A sleeve carrier contains a plurality of ports, which allows a current generated by an electrical stimulation device to flow through the cable to the cathode where it is evenly distributed through the ports to the bone tissue. The sleeve can be slipped onto a fracture fixation device, such as a compression hip screw, and is located on the device such that the sleeve containing the cathode lies across the fracture site.

The known cathode assembly has the disadvantage that it requires a percutaneous wired connection between the electrical bone growth stimulation apparatus and the cathode assembly such that the risk of infections is increased. A further disadvantage is that mounting the cathode assembly on the fixation device in the course of a surgery is a rather complicated procedure such that the risk of a surgery trouble or a surgery mistake is also increased.

U.S. Pat. No. 4,421,115 discloses an electrification attachment for an osteosynthesis implant, which permits electric stimulation of tissue and specifically bone tissue to which an osteosynthesis plate or a bone nail has been attached. The attachment provides electrical energy by induction from an external induction coil. A support body is provided for attaching association with the osteosynthesis implant. At least one induction coil is embedded in, or secured to the body. Electrodes are connected to the windings of the coil, one of which is connectable with a conductive portion of the osteosynthesis implant, the other electrode being exposed to bone tissue of the patient. However, the disclosed electrification attachment has the disadvantage that due to the geometry of the electrode being exposed to the bone tissue only a rather weak electric field can be applied to the damaged bone region such that the bone healing effect is comparatively small.

There may be a need for providing an osteogenesis stimulation device, which can be easily inserted together with a bone stabilizing implant and which provides for an improved bone healing effect.

SUMMARY OF THE INVENTION

According to a first aspect of the invention there is provided a device for stimulating the osteogenesis of a traumatized bone being fixed by means of a bone stabilizing implant. The osteogenesis stimulation device comprises (a) a first component part comprising a first electrode, (b) an isolating element, which is mounted at the first component part, (c) a second component part comprising a second electrode, which is mounted at the isolating element such that the first electrode and the second electrode are electrically isolated from each other, and (d) a power generation unit, which is electrically coupled both to the first electrode and to the second electrode. Thereby, the first component part is designed in such a manner that the osteosynthesis stimulation device can be attached to the implant such that the second component part intrudes in a region defined by a trauma within the bone.

This aspect of the invention is based on the idea that the device for stimulating osteogenesis is not used for fixing the traumatized bone. This means that it is not necessary that the device is adapted for receiving mechanical tensions or mechanical stresses. In other words, when designing the device one can focus on the electrical properties in order to provide for an improved osteogenesis.

It has to be mentioned that the term "traumatized bone" describes all types of bone injuries such as in particular fractures.

In order to provide for an effective bone healing stimulation the implant may be electrically connected to the first electrode such that an electric field between the second electrode on the one hand and the first electrode connected to the implant on the other hand penetrates the whole region of the trauma as uniform as possible. In this respect is pointed out that a homogenization of the electrical field within the traumatized region may require the use of a conductive implant. However, since bone stabilization implants are typically made from titanium and/or steel the implants are electrically conductive anyway. However, it has to be mentioned that the described osteogenesis stimulation device may also be used in connection with implants made from a non-conductive material or comprising a non-conductive material.

It has to be further mentioned that the first and/or the second electrode may be formed either integrally with the first and/or the second component part or the first and/or the second electrode may be formed at outer surfaces of the first and/or the second component part.

According to an embodiment of the invention the power generation unit is integrated within the first component part and/or the second component part. This has the advantage that the osteogenesis stimulation device may be realized within a compact configuration such that the implant of such a compact device does not complicate a surgery wherein a traumatized or broken bone is fixed in its anatomical correct position by means of an appropriate bone stabilizing implant.

The power generation unit may be a self-supply or self-contained generator having an energy-storage component such as an accumulator or a battery.

Preferably, the first component part accommodates the power generation unit because when realizing the osteogenesis stimulation device typically the first component part will be bigger than the second component part. This means, that within the first component part there will be more space than within the second component part.

According to a further embodiment of the invention the power generation unit is adapted to receive energy from a power transmission unit wirelessly. This has the advantage that the electric energy needed for a proper operation of the osteogenesis stimulation device may be supplied from outside the patient's body without requiring a percutaneous connection between the power transmitting unit and the power generation unit.

According to a further embodiment of the invention the power generation unit comprises a solenoid coil. This provides the advantage that the wireless power transmission may be achieved by an inductive coupling between the power transmitting unit and the power generation unit. In this context the power generation unit may also be denominated a power-receiving unit.

This may further provide the advantage that the power generation unit can be realized in a very simple but effective way. Apart from the solenoid or magnetic coil and the corresponding electrical contacts between a first and a second terminal of the coil and the first and second electrode, respectively, no additional electrical and/or mechanical components are necessary for realizing the power generation unit. Therefore, the power generation unit may be realized within of a very compact design such that the described osteogenesis stimulation device is suitable for a variety of different applications in the field of osteosynthesis.

In this respect it is clear that when an inductive coupling is used for transmitting electromagnetic energy to the power generation unit, the electrical field being present within the region of the trauma is an alternating electrical field. Thereby, the frequency of the alternating electrical field may be adjusted in such a manner that an optimal osteogenesis stimulation effect is achieved.

According to a further embodiment of the invention the first component part is adapted to be accommodated at least partially within an opening of the bone stabilizing implant. This provides the advantage that the osteogenesis stimulation device may be used in connection with many different types and sizes of bone stabilizing implants without complicating surgeries wherein an appropriate implant is inserted into a patient's body for osteosynthesis purposes. Preferably, the first component part may be accommodated fully within the opening such that the osteogenesis stimulation device does not cause any edges or corners protruding from the bone stabilizing implant when being implanted.

According to a further embodiment of the invention the opening is a through hole formed within the bone stabilizing implant. This may provide the advantage that in particular when the bone stabilizing implant is a plate, conventional through holes may be used for accommodating the osteogenesis stimulation device. Since a bone stabilizing implant typically is provided with a plurality of such conventional through holes for inserting bone fixing screws there are many possibilities in order to spatially position the osteogenesis stimulation device at the most appropriate location with respect to the bone trauma. In this respect it is mentioned that typically not all through holes of a plate are used for inserting screws such that using the described osteogenesis stimulation device does not mean that the bone stabilizing implant cannot be properly fixed to the broken bone portions.

A further advantage of this embodiment is that conventional implants may be used in order to provide a bone stabilizing implant and in particular a bone stabilizing plate with an osteogenesis stimulation device. Further, most of the conventional implants may be used without performing modifications on these implants.

The possibility of employing conventional implants further provides the advantage that the attachment of the described osteogenesis stimulation device to the implant does not cause a biomechanical weakening of the implant. Such a biomechanical weakening frequently occurs with conventional osteogenesis stimulation implants wherein coils and/or other electronic components are incorporated within the implant.

According to a further embodiment of the invention the first component part comprises a shape corresponding to the outer contour of a screw head. This has the advantage that the osteogenesis stimulation device may be inserted into any opening of the implant, which opening is shaped in such a manner that a conventional fixing screw may be inserted.

According to a further embodiment of the invention the first component part comprises an external thread. This advantageously allows for a reliable and spatially very stable attachment of the osteogenesis stimulation device to the implant. Thereby, it is clear that also the adequate opening within the implant has to be provided with an internal thread corresponding to the thread of the described device.

According to a further embodiment of the invention the first component part is adopted such it can be attached to the implant by means of a snapping mechanism. The snapping mechanism may comprise a resilient member, which engages into an adequately formed engagement element when the osteogenesis stimulation device is mounted to the bone stabilizing implant. Preferably, the resilient member may be formed at the first component part and the engagement element may be formed at the implant. However, it is also possible that the resilient member may be formed at the implant and the engagement element may be formed at the first component part, respectively.

The provision of a snapping mechanism has the advantage that the described osteogenesis stimulation device may be attached to the bone stabilizing implant very easily. In particular, if the implant is a bone stabilizing plate the device may be attached thereto after the plate has been fixed to the patient's traumatized bone. This has the beneficial effect that a surgery procedure wherein a bone stabilizing implant is inserted does not differ from a corresponding surgical procedure wherein a conventional body implant without any bone healing stimulation device is incorporated into the patient's body.

According to a further embodiment of the invention the second component part comprises the shape of a screw bolt or to a screw shaft. Thereby, the length of the screw bolt should be selected in an appropriate manner depending on the shape, the width and/or the depths of the trauma.

According to a further embodiment of the invention the second component part comprises a spike. This may provide the advantage that the stimulating electrical field can penetrate deeply into the trauma without disproportional disturbing the osteogenesis because of the spatial presence of a mechanical member.

According to a further aspect of the invention there is provided a medical system for stimulating the osteogenesis of a traumatized bone, the medical system comprising (a) a bone stabilizing implant, which is adapted to be fixed to the traumatized bone, and (b) a device according to any one of the embodiments as described above.

This further aspect of the invention is also based on the idea that the osteogenesis stimulation device may be solely adapted for providing an optimal electric and/or magnetic field within the region of the bone trauma. Of course, the medical system may also comprise fixing elements like screws or the like in order to provide for a tight mechanical contact between the implant and the traumatized bone. However, it is not necessary that the osteogenesis stimulation device contributes to tight mechanical contact. Therefore, the described device may be optimized with respect to the electric properties.

In this respect it has to be mentioned that a direct current (DC) voltage or alternatively an alternating current (AC) voltage may be applied to the first respectively to the second electrode. Thereby, it is clear that according to the principles of electrodynamics an alternating electric field automatically creates an alternating magnetic field. Therefore, in case of employing an AC voltage both an electric field and a magnetic field may promote the osteogenesis.

According to an embodiment of the invention the bone stabilizing implant is a plate or a nail. This has the advantage that these types of implants are typically big enough to accommodate the osteogenesis stimulation device. Therefore, adjustments, backfittings and/or modifications to the corresponding implants are not necessary in order to provide the implants with the described osteogenesis stimulation device.

It has to be pointed out that different types of nails are appropriate for being provided with the osteogenesis stimulation device. For instance intramedullary nails, which are supposed to be driven into the bone marrow, or nails, which are inserted transverse into a broken or traumatized bone, may be suitable for being inserted into a patient's body together with the described osteogenesis stimulation device.

In this respect it has to be further pointed out that the described osteogenesis stimulation device may also be used for other types of implants, which may be used for various types of bone fractures.

According to a further embodiment of the invention the medical system further comprises an insertion element, which is adapted to accommodate the device and which is further adapted to be inserted into an opening of the bone stabilizing implant by means of a snapping mechanism. The use of such an insertion element has the advantage that the osteogenesis stimulation device may be inserted easily into the implant by means of a simply movement of an operators hand.

As has already been described above in connection with a snapping mechanism provided directly in between the implant and the first component part also a snapping mechanism provided in between the implant and the insertion element has the advantage that the described osteogenesis stimulation device may be attached to the bone stabilizing implant very easily. In particular, if the implant is a bone stabilizing plate, the insertion element and/or the osteogenesis stimulation device may be attached thereto after the plate has been fixed to the patient's traumatized bone.

The use of an insertion element may further advantageously be used in order to provide a modular system wherein one type of osteogenesis stimulation device may be inserted into different implants having different shaped openings. Thereby, the insertion element may represent an adaptor element between a standard osteogenesis stimulation device and different implant openings.

It has to be mentioned such an insertion element is disclosed in detail with United States Publication No. US2004/0254578, the disclosure of which is hereby incorporated herein by reference.

It has to be noted that embodiments of the invention have been described with reference to different subject matters. In particular, some embodiments have been described with reference to an osteogenesis stimulation device whereas other embodiments have been described with reference to a medical system. However, a person skilled in the art will gather from the above and the following description that, unless other notified, in addition to any combination of features belonging to one subject matter also any combination between features relating to different subject matters, in particular between features describing the osteogenesis stimulation device and features describing the medical system is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
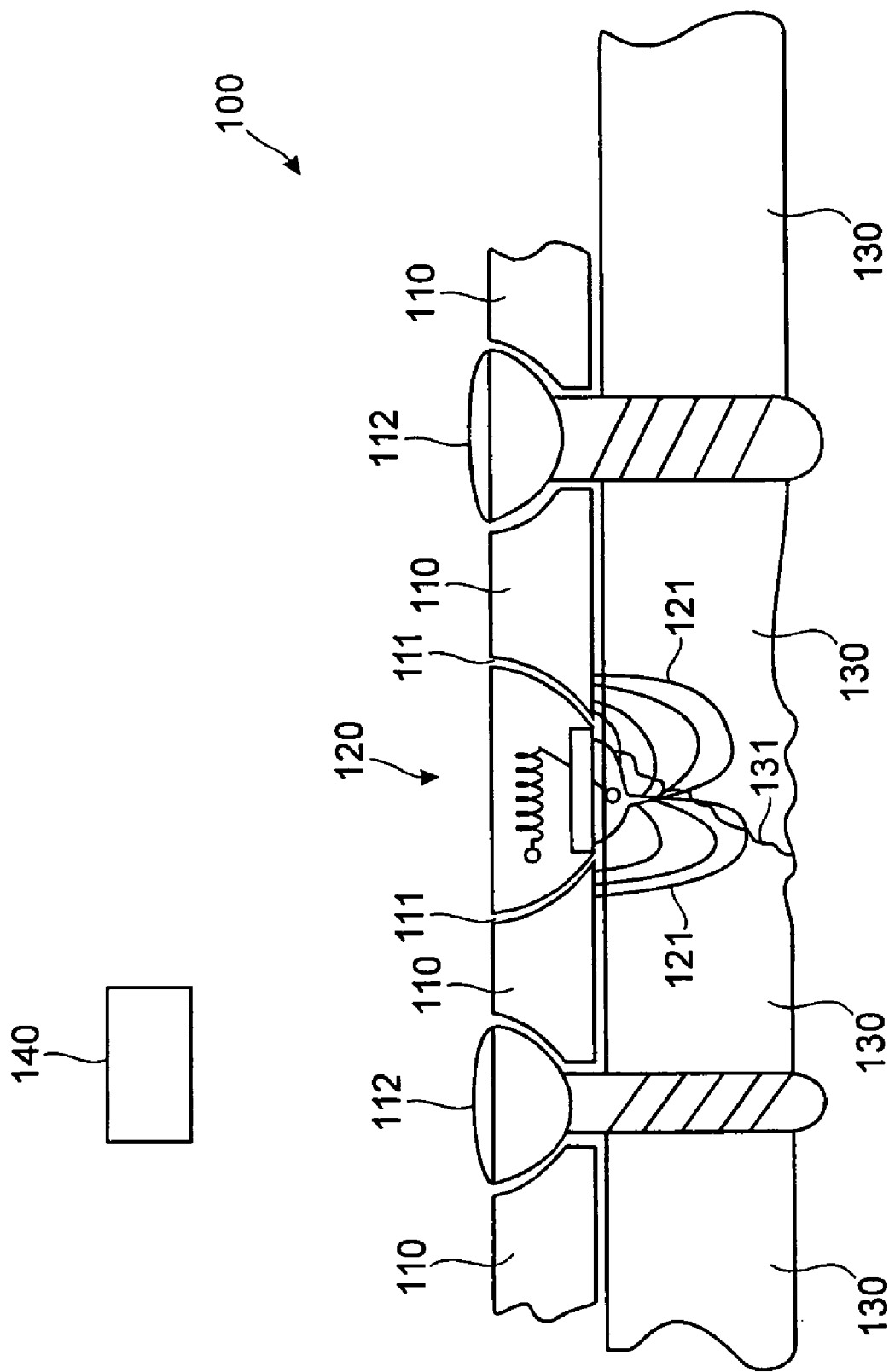
FIG. 1 shows a medical system comprising an osteogenesis stimulation device mounted to a bone stabilizing plate.

The illustration in the drawing is schematically. It is noted that in different figures, similar or identical elements are provided with the same reference signs or with reference signs, which are different from the corresponding reference signs only within the first digit.

FIG. 1 shows a medical system 100 comprising an osteogenesis stimulation device 120 mounted to a bone stabilizing implant 110, which according to the embodiment described here is a bone stabilizing plate 110. The plate 110 is fixed by means of fixing screws 112 to different sections of a broken bone 130, which comprises a fissure 131 representing a special form of a bone trauma respectively a bone fracture.

The osteogenesis stimulation device 120 is accommodated within a central opening of the plate 110. The central opening may be any type of through hole, which for instance may also be used for inserting a fixing screw 112. Thereby, the osteogenesis stimulation device 120 is formed in such a manner that its outer surface complementary corresponds to the inner shape of the central opening, which on the upper side of the plate 110 is limited by an edge 111 having a rounded shape.

Preferably, the osteogenesis stimulation device 120 can be attached to the plate 110 by means of a snapping mechanism (not depicted). The snapping mechanism may comprise a resilient member, which engages into an adequately formed engagement element when the osteogenesis stimulation device 120 is mounted to the plate 110. The use of a snapping mechanism has the advantage that the osteogenesis stimulation device 120 may be attached within the central opening very easily. In particular, the device 120 may be attached thereto after the plate 120 has been fixed to the patient's traumatized bone.

Figure 2:
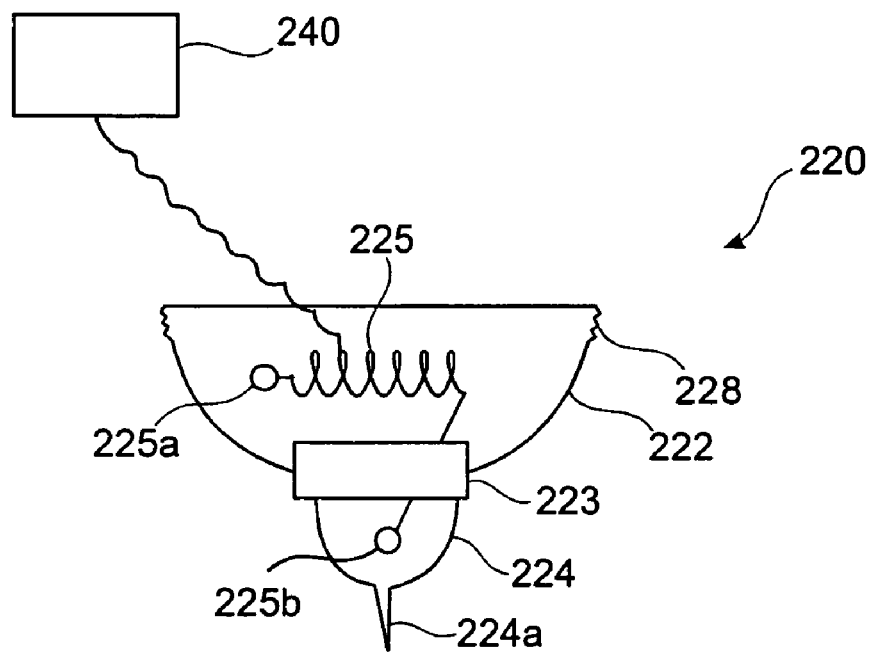
FIG. 2 shows an enlarged illustration of the osteogenesis stimulation device shown in FIG. 1.

The osteogenesis stimulation device 120, which will be described in detail later on with reference to FIG. 2, is adapted to generate an alternating electric field penetrating into the region of the bone fissure 131. The alternating electric field is schematically illustrated by means of streamlines 121. Of course, according to the principles of electro dynamics the alternating electrical field is accompanied by a magnetic field.

The osteogenesis stimulation device 120 is powered by a power transmitting unit 140, which is inductively coupled with the device 120 in order to provide the osteogenesis stimulation device 120 with the required energy.

FIG. 2 shows an enlarged illustration of the osteogenesis stimulation device 120, which is now denominated with reference numeral 220. The osteogenesis stimulation device 220 comprises a first component part 222 representing a first electrode. At the first component part 222 there is provided an isolating element 223. The isolating element 223 is made from a biologically compatible, tissue-compatible plastic such as polyethylene or a carbon-fluoropolymer. The isolating element is necessary in order to provide a galvanic separation between the first electrode 222 and a second component part 224 representing a second electrode. In order to generate the stimulating electrical field deeply within the region of a bone trauma the second electrode comprises a spike 224a.

Within the first component part 222 there is accommodated a power generation unit 225, which according to the embodiment described here is a simple magnetic coil. The coil 225 is adapted to inductively receive energy provided by the power-transmitting unit 240. In order to generate an alternating electric field between the first electrode 222 and the second electrode 224 a first terminal 225a is electrically coupled with the first electrode 222 and a second terminal 225b is electrically coupled with the second electrode 224. Since the spike 224a is a part of the second electrode 224 a the alternating electric field penetrates deeply into the traumatized region respectively into the fissure 131 formed in between the two bone parts 130 shown in FIG. 1.

It has to be mentioned that the region wherein the alternating electric field is present may be enlarged when (a) the plate 110 is made from a conductive material and (b) the plate 110 is electrically connected to the first electrode 222. In this case, the plate 110 represents an equipotential or isoelectric member being at the same potential as the first electrode 222. Therefore, the streamlines 121 of the electrical field are also formed in between the second electrode 224 and the plate 110 (see FIG. 1).

Figure 3:
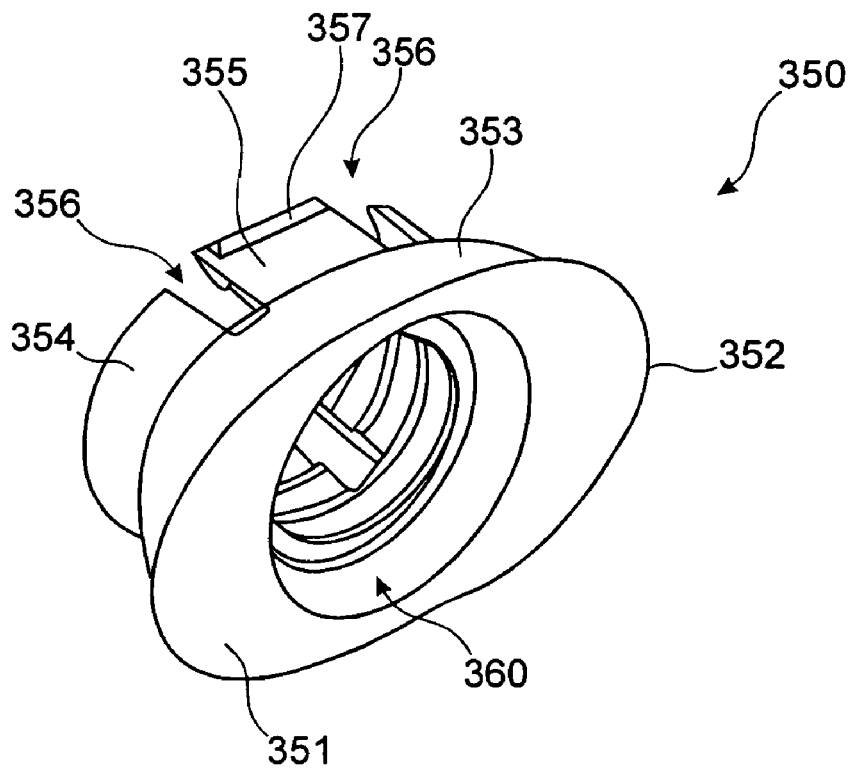
FIG. 3 shows a perspective view of an insertion element for accommodating the osteogenesis stimulation device as shown in FIG. 2.

FIG. 3 shows a perspective view of an insertion element 350, which may be used in conjugation with the osteogenesis stimulation device 220. Reference numeral 351 refers to the surface of the insertion element 350 having a circumference 352 that meets with the edge 111 of the central opening of the plate 110. In the preferred embodiment described here, a tapered spherical surface 353 extends downwardly from surface 351 and is shaped so as to have a complementary surface contact with the inner surface of the central opening of the plate 110. A semicircular extension 354 extends downwardly from surface 353 and is in conforming contact without any significant play with the inner area of the central opening of the plate 110.

The insertion element 350 comprises a through hole 360 which is formed in such a manner that the inner surface of the hole 360 complementary fits to the outer surface of the osteogenesis stimulation device 220 shown in FIG. 2. The device 220 can be inserted into the insertion element 350 by screwing the device 220 into the through hole 360. Therefore, the device 220 is provided with an outer screw thread 228 and the through hole 360 is provided with an inner screw thread (not depicted).

The insertion element 350 comprises a resilient extension 355 on each side. According to the preferred embodiment shown here, two slots 356 are assigned to each resilient extension 355. Each extension 355 has on its lower edge a projecting rim 357 facing outward.

The extension 355 is also to a certain extent, flexible. When the insertion element 350 is inserted into the central opening of the plate 110, the extensions 355 are pressed slightly inward. Once the insertion element 355 has been completely inserted, the projecting rim 357 snaps into a corresponding shoulder (not depicted) formed within the central opening of the plate 110 and locks the insertion element 350 within the plate 110.

It should be noted that extension 355 and with it the projecting rim 357 need not necessarily be arranged as two extensions 355 on the opposing longer sides of the insertion element 350. The design can also include resilient extensions on the narrow sides of an insertion element 350, i.e. corresponding to the location of the semicircular cylindrical extensions 354. The extensions 355 can also be arranged in an alternating manner. Further, the insertion element 350 can also be provided with only one or with more than two extensions.

It should be noted that the term "comprising" does not exclude other elements and the term "a" or "an" does not exclude a plurality. Also elements described in association with different embodiments may be combined. It should also be noted that reference signs in the claims should not be construed as limiting the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for stimulating the osteogenesis of a traumatized bone being fixed by means of a bone stabilizing implant, the device comprising:
   a first component part comprising a first electrode,
   an isolating element, which is mounted at the first component part,
   a second component part comprising a second electrode, which is mounted at the isolating element such that the first electrode and the second electrode are electrically isolated from each other, and
   a power generation unit, which is electrically coupled both to the first electrode and to the second electrode, wherein the first component part is designed to be attached to the implant in such a manner that the second component part intrudes in a region defined by a trauma of the bone.

2. The device according to claim 1, wherein the power generation unit is integrated within the first component part and/or the second component part.

3. The device according to claim 1, wherein the power generation unit is adapted to receive energy from a power transmitting unit wirelessly.

4. The device according to claim 3, wherein the power generation unit comprises a solenoid coil.

5. The device according to claim 1, wherein the first component part is adapted to be accommodated at least partially within an opening of the bone stabilizing implant.

6. The device according to claim 5, wherein the opening is a through hole formed within the bone stabilizing implant.

7. The device according to claim 1, wherein the first component part comprises a shape corresponding to the outer contour of a screw head.

8. The device according to claim 1, wherein the first component part comprises an external thread.

9. The device according to claim 1, wherein the first component part is adapted such it can be attached to the implant by means of a snapping mechanism.

10. The device according to claim 1, wherein the second component part comprises the shape of a screw bolt or a screw shaft.

11. The device according to claim 1, wherein the second component part comprises a spike.

12. A system for stimulating the osteogenesis of a traumatized bone, the medical system comprising:
   a bone stabilizing implant, which is adapted to be fixed to the traumatized bone, and
   a first component part comprising a first electrode,
   an isolating element, which is mounted at the first component part,
   a second component part comprising a second electrode, which is mounted at the isolating element such that the first electrode and the second electrode are electrically isolated from each other, and
   a power generation unit, which is electrically coupled both to the first electrode and to the second electrode, wherein the first component part is designed to be attached to the implant in such a manner that the second component part intrudes in a region defined by a trauma of the bone.

13. The medical system according to claim 12, wherein the bone stabilizing implant is a plate or a nail.

14. The medical system according to claim 12, further comprising:
   an insertion element,
      which is adapted to accommodate the device and
      which is further adapted to be inserted into an opening of the bone stabilizing implant by means of a snapping mechanism.

15. A method for stimulating the osteogenesis of a fractured traumatized bone comprising:
   implanting a fracture fixation device;
   inserting an electrical stimulation element into the opening of the fracture fixation device, the electrical stimulation element having a body with a first electrode in a first body portion and a second electrode in a second body portion, the first and second body portions being electrically isolated, the first body portion contacting the fracture fixation device and the second body portion intruding in a region defined by a trauma of the bone; and
   connecting an electrical current generating source to the first and second electrodes.

16. The method as set forth in claim 15 wherein the current is an alternating current.

17. The method as set forth in claim 15 further comprising inserting an insert having a through-bore into the opening in the fracture fixation device and inserting the electrical stimulation element into the through-bore of the insert.

18. The method as set forth in claim 17 wherein the insert is snapped into the opening of the fracture fixation device and held therein by resilient extensions on the insert.

19. The method set forth in claim 18 further comprising screwing the electrical stimulation element into the through-bore of the insert.

* * * * *

UNITED STATES PATENT AND TRADEMARK OFFICE
CERTIFICATE OF CORRECTION

PATENT NO.          : 7,890,179 B2
APPLICATION NO.     : 11/583325
DATED               : February 15, 2011
INVENTOR(S)         : Markus Wiegmann and Christian Lutz It is certified that error appears in the above-identified patent and that said Letters Patent is hereby corrected as shown below:

Title Page, Item (57) Abstract, line 17, after "described above" delete "is".
Column 1, line 39, "coil being electrically" should read --coil are electrically--.
Column 1, line 41, "shaft are filled" should read --shaft is filled--.
Column 2, line 6, "respectively" should read --respective of--.
Column 2, line 26, "risk of a surgery" should read --risk of surgery--.
Column 2, line 35, "secured to the body" should read --secured to, the body--.
Column 3, line 14, "respect is pointed" should read --respect it is pointed--.
Column 3, line 42, "This means, that" should read --This means that--.
Column 3, line 67, "realized within of a" should read --realized within a--.
Column 5, line 22, "to a screw shaft" should read ---a screw shaft--.
Column 5, line 50, "applied to the first respective to the" should read --applied respectively to the first and to the--.
Column 6, line 9, after "element" delete ",".
Column 6, line 15, "simply movement of an operators" should read --simple movement of an operator's--.

Signed and Sealed this
Twentieth Day of March, 2012

David J. Kappos
*Director of the United States Patent and Trademark Office*